United States Patent [19]

Shaw

[11] Patent Number: 5,218,147
[45] Date of Patent: Jun. 8, 1993

[54] STABLE POLYSULFIDES AND PROCESS THEREFOR

[75] Inventor: James E. Shaw, Bartlesville, Okla.

[73] Assignee: Phillips Petroleum Company, Bartlesville, Okla.

[21] Appl. No.: 875,489

[22] Filed: Apr. 29, 1992

Related U.S. Application Data

[63] Continuation-in-part of Ser. No. 833,264, Feb. 10, 1992, abandoned.

[51] Int. Cl.$^5$ .............................................. C07C 319/26
[52] U.S. Cl. ......................................... 568/21; 568/19
[58] Field of Search .................... 568/19, 21; 208/207, 208/236

[56] References Cited

U.S. PATENT DOCUMENTS

| | | | |
|---|---|---|---|
| 2,059,075 | 5/1936 | Yabroff et al. | 208/236 |
| 2,496,508 | 6/1946 | Watson et al. | 568/19 |
| 2,571,157 | 10/1951 | Olin et al. | 269/609 |
| 2,575,989 | 9/1949 | Arundale et al. | 208/204 |
| 2,794,769 | 6/1957 | Jezl | 196/32 |
| 2,862,804 | 12/1958 | Petty | 44/76 |
| 3,308,166 | 3/1967 | Biensan et al. | 260/608 |
| 4,156,641 | 5/1979 | Frame | 208/207 |
| 4,876,389 | 10/1989 | Gongors | 568/26 |

FOREIGN PATENT DOCUMENTS 58-140063  2/1982  Japan ..................... 149/12

*Primary Examiner*—Marianne M. Cintins
*Assistant Examiner*—Margaret J. Page
*Attorney, Agent, or Firm*—Lucas K. Shay

[57] ABSTRACT

A process for preparing a stable polysulfide compound, synthesized by reacting a mercaptan with elemental sulfur in the presence of a basic catalyst, having reduced mercaptan sulfur content is provided which comprises contacting the crude polysulfide with an alkylene oxide in the presence of a tetraalkylammonium hydroxide or a basic inorganic catalyst in a solvent.

31 Claims, No Drawings

STABLE POLYSULFIDES AND PROCESS THEREFOR

This application is a continuation-in-part of application Ser. No. 07/833,264, filed on Feb. 10, 1992, now abandoned.

FIELD OF THE INVENTION

The present invention relates to stable polysulfide compounds and to a process for producing the stable polysulfide compounds.

BACKGROUND OF THE INVENTION

Organic polysulfides and particularly dialkyl polysulfides such as tetra- and penta-sulfides have been found useful for many purposes such as additives for elastomers, antioxidants for lubricating oils, intermediates for the production of organic chemicals, insecticides, germicides and as an additive to diesel fuels to improve the cetane number and ignition qualities of these fuels. These compounds have also been found useful in the compounding of extreme pressure lubricants and in the acceleration of rubber treating processes.

Such polysulfide compounds can be prepared by reacting mercaptans with elemental sulfur in the presence of a basic catalyst. For example, Biensan et al (U.S. Pat. No. 3,308,166) discloses that polysulfides can be prepared from a mercaptan and sulfur catalyzed by an amine using an alcohol promoter.

A conventional process for producing a polysulfide compound such as di-t-dodecyl polysulfide is to react a mercaptan such as t-dodecylmercaptan with elemental sulfur in the presence of triethylamine as catalyst. However, the polysulfide thus prepared is associated with some unreacted mercaptans and residual $H_2S$ contributing to unpleasant odor. Additionally, possibly because of the unreacted mercaptans and the amine catalyst, the product always becomes very unstable, i.e. the product turns cloudy, probably due to degradation of the polysulfide causing precipitation of sulfur. The instability along with the unpleasant odor greatly reduce the desirability and utility of the polysulfide product.

There is therefore a need to remove the odor associated with the product and to stabilize the product. Kamii et al (Japanese Application 58-140,063) discloses a process for deodorizing dialkyl polysulfides by contacting the polysulfide-bearing fluid with 1,2-epoxy compounds. The 1,2-epoxy compounds apparently react directly with the unreacted mercaptan and hydrogen sulfide, thereby producing a product with reduced odor. Excess 1,2-epoxy compounds are reportedly removed by conventional methods, such as vacuum distillation.

However, Kamii et al does not disclose any process for stabilizing a polysulfide compound. Additionally, the process disclosed in Kamii et al produces a product that still has such high a mercaptan level that it would contribute the instability of the polysulfide product. It would therefore be a significant contribution to the art to develop a process for the stabilization of such a polysulfide product so that the product is made more useful for industrial uses.

SUMMARY OF THE INVENTION

An object of the present invention is to develop a process to stabilize a polysulfide compound. Another object of the present invention is to reduce the odor associated with the polysulfide compound. A further object of the present invention is to reduce unreacted or residual sulfur-containing compounds contaminating the polysulfide. Yet another object of the present invention is to prepare a polysulfide that is stable and deodorized.

An advantage of the present invention is the reduction of the concentration of the unreacted mercaptans to as low as less than 1 ppm while maintaining the polysulfide in high yield. Other advantages and features will become more apparent as the invention is more fully disclosed in the following disclosure and claims.

According to the present invention, a process for stabilizing and deodorizing a polysulfide prepared by reacting a mercaptan with sulfur catalyzed by a basic catalyst is discovered which comprises contacting the polysulfide with an alkylene oxide in the presence of a basic inorganic catalyst in a solvent.

According to a further embodiment of the invention it is provided a process for stabilizing and deodorizing a polysulfide, prepared by reacting a mercaptan with sulfur catalyzed by a basic catalyst, which comprises contacting the polysulfide with an alkylene oxide in the presence of a tetraalkylammonium hydroxide in a solvent.

DETAILED DESCRIPTION OF THE INVENTION

The process for the preparation of a stabilized polysulfide compound having reduced odor involves contacting a polysulfide product, which can be produced by a catalytic reaction of a mercaptan and elemental sulfur, with an alkylene oxide in the presence of a basic inorganic catalyst in a solvent.

The process for the preparation of a stabilized compound having reduced odor further involves contacting a polysulfide product with an alkylene oxide in the presence of a tetraalkylammonium hydroxide in a solvent.

The polysulfide compound of the present invention has a general formula of $RS_nR'$ with R and R' can be the same or different and are alkyl radicals having about 1 to about 20 carbon atoms, and n is an integer of 2 to 10. Preferably R and R' are alkyl radicals having about 3 to about 15 carbon atoms and n is 3 to 8. Most preferably, R and R' are alkyl radicals having 9 to 12 carbon atoms and n is 3 to 6.

The polysulfide can be prepared by the reaction of mercaptans and elemental sulfur catalyzed by a basic catalyst. The reaction is depicted as $RSH + R'SH + (n-1)S \rightarrow RS_nR' + H_2S$ where R, R' and n are the same as those described above. The reaction can be carried out under any reaction condition, in any suitable reaction vessel. The basic catalyst can be a metal hydroxide such as sodium hydroxide, a metal oxide or a metal salt such as MgO and $NaCO_3$, and an amine such as triethylamine. Generally, one of the reactants, either the mercaptan or sulfur, is slowly added to the other reactant in the presence of a basic catalyst. The sulfur, upon addition, readily dissolves in the solution. Mixing of the solution and/or operating at higher than ambient temperatures will enhance the reaction rate. The amount of sulfur added depends on the desired sulfur content of the polysulfide product. For an average sulfur content of n-sulfurs per polysulfide molecule, (n-1) moles of sulfur must be added and 1 mole of hydrogen sulfide will be released per 2 moles of mercaptans reacted. The weight of the basic catalyst as a percentage of the weight of mercaptan should be 0.05 to 5%, preferably 0.1 to 2.0%, and most preferably 0.2 to 1.0%.

Following completion of the reaction, residual hydrogen sulfide may be removed from the crude polysulfide product by either an inert gas purge or by vacuum stripping. When using an inert gas purge, preferably gases are nitrogen and air.

Following the removal of most residual hydrogen sulfide, the crude polysulfide product is contacted with an alkylene oxide and a basic inorganic catalyst in a solvent. The alkylene oxide can have 1 to about 10 carbon atoms. The presently preferred alkylene oxide has 1 to 4 carbon atoms and is selected from the group consisting of ethylene oxide, propylene oxide, 1,2-butylene oxide, 1,3-butylene oxide, and isobutylene oxide.

The basic inorganic catalyst useful in the present invention can be employed as it is, supported on a solid support such as all forms of alumina and silica, or an aqueous solution. The presently preferred basic inorganic catalyst is selected from the group consisting of $LiOH$, $NaOH$, $KOH$, $Ca(OH)_2$, $Mg(OH)_2$, $Na_2O$, $MgO$, $CaO$, $NaHCO_3$, $Na_2CO_3$, $CaCO_3$, calcium phenoxide, barium phenoxide, $R''ONa$, $R''SNa$, $R''O(CH_2CH_2O)mNa$, $R''S(CH_2CH_2O)mNa$, and mixtures thereof, where $R''$ is a $C_1$-$C_6$ alkyl radical and m is an integer between 1 and 15. The presently most preferred base is NaOH because of its availability and cost.

Following the removal of most residual hydrogen sulfide, the crude polysulfide product can also be contacted with an alkylene oxide and a tetraalkylammonium hydroxide in a solvent. Suitable alkylene oxides are the same as those described above. Presently preferred tetraalkylammonium hydroxide is tetramethylammonium hydroxide, tetraethylammonium hydroxide and tetrapropylammonium hydroxide. The presently most preferred tetraalkylammonium hydroxide is tetramethylammonium hydroxide.

The solvent must be miscible with the basic inorganic catalyst or tetramethylammonium hydroxide employed. It can be water, an ether or an alcohol. Suitable solvents include methanol, ethanol, propanol, tetrahydrofuran, and other similar oxygen-containing solvents. Methanol is the presently preferred solvent because of its combined solubilization properties, high vapor pressure, and lower density thus providing a greater density contrast between the alcohol-phase and the polysulfide phase, thereby simplifying the phase separation.

The amount of alkylene oxide, base, tetraalkylammonium hydroxide and solvent for the present invention is the amount that is effective to convert the crude polysulfide to a stable product having reduced odor and suitable for long term storage. The molar ratio of the alkylene oxide to the polysulfide is from about 0.001:1 to about 50:1, preferably from about 0.005:1 to about 2:1, and most preferably from 0.01:1 to 1:1. The molar ratio of the basic inorganic catalyst to the polysulfide ranges from about 0.001:1 to about 2:1, preferably from about 0.005:1 to about 1:1, and most preferably from 0.01:1 to 0.1:1. The molar ratio of the solvent to the polysulfide is from about 0.001:1 to about 20:1, preferably from about 0.01:1 to about 10:1, and most preferably from 0.02:1 to 1:1. The molar ratio of the tetraalkylammonium hydroxide to the polysulfide is from about 0.001:1 to about 2:1, preferably from about 0.05:1 to about 1:1, and most preferably from 0.01:1 to 0.1:1.

The process of the invention can be carried out in any suitable vessel. It is preferred to carry out in the same vessel where the crude polysulfide is prepared. Though the basic inorganic catalyst or the tetramethylammonium hydroxide is generally added to the crude polysulfide first, the order of adding the alkylene oxide and either tetraalkylammonium hydroxide or basic inorganic catalyst generally does not significantly affect the purity and stability of the final product. However, it is preferred that the basic inorganic catalyst or the tetraalkylammonium hydroxide in a solvent be mixed with the crude product first. Generally, following the addition of the basic inorganic catalyst or the tetraalkylmethylammonium hydroxide to the crude polysulfide, the mixture is mixed by a suitable means such as stirring and heated to about 50°-150° C., preferably about 60°-100° C., most preferably 65°-80° C., followed by the addition of alkylene oxide. The heating step can also be carried out after the alkylene oxide is added to the mixture.

The mixture is then further heated at the same temperature range described above for about 10 minutes to about 10 hours, preferably about 30 minutes to about 5 hours, most preferably 1 hour to 3 hours. Upon completion of heating, nitrogen sparge into the mixture can be initiated at about 1 to about 10 standard cubic feet per hour for about 10 minutes to about 5 hours.

The heated mixture can be further purified if necessary. This is usually done by conventional separation means such as filtration to remove any impurities or by distillation.

The process of the invention can also be carried out continuously. For example, the contacting of the alkylene oxide and either basic inorganic catalyst or tetraalkylammonium hydroxide with the crude polysulfide can be done by employing continuous stir tank reactors connected in series, packed columns or towers in which the alkylene oxide and either basic inorganic catalyst or tetraalkylammonium hydroxide are supported on a solid support, and other continuous flows that are readily within the realm of one skilled in the art.

The following examples are provided to further illustrate the practice of the invention and are not intended to limit the scope of the invention or the claims.

EXAMPLE I

This example illustrates the preparation of di-t-nonyl polysulfide having an average of 5 sulfurs.

To a 1 liter autoclave reactor which has been flushed with nitrogen ($N_2$), it was added a solution of 599 g (3.74 mole) t-nonyl mercaptan and 3.8 g (0.037 mole) triethylamine. The autoclave was heated to 30° C. and the contents were stirred rapidly (1000 rpm). Sulfur (240 g, 7.49 mole) in a 300 ml stainless steel bomb equipped with an internal thermocouple was melted by heating at 120°-135° C. under $N_2$. With the melted sulfur at 135° C., the $N_2$ pressure above the sulfur in the bomb was increased to 200 psi, and the valve and tubing between the bomb and autoclave were heated so sulfur would not solidify in them during the sulfur transfer. The liquid sulfur was added over a 2 minute time period so as to avoid solidification of sulfur in the tube that went through the autoclave body. The addition of the liquid sulfur over a 2 minute time period caused the autoclave temperature to increase from 30° c. to the desired process temperature of 45° C.

When the sulfur addition was completed, the autoclave pressure had increased to 150 psi due to $H_2S$ evolution. The autoclave pressure was then decreased to 60 psi by the controlled venting of $H_2S$ for about 0.5 hour. At this point, $H_2S$ was removed by pressurizing the autoclave with $N_2$ to 100 psi and then venting to 60 psi. This was repeated 3 more times over a 0.5 hour time period and the pressure (mainly due to N$_2$) was allowed to decrease near atmospheric whereupon the system was opened to a vent line. Heating at 45° C. with rapid stirring (1000 rpm) was continued for an additional 1.5 hours (total time after addition of all sulfur was 2.5 hours). Nitrogen was then bubbled (2 std cubic ft/hr) through the reaction mixture at 45° C. with rapid stirring (1000 rpm) for 4 hours to remove most (but not all) hydrogen sulfide and triethylamine.

To 775 g of the crude di-t-nonyl polysulfide prepared by the above process was added 4.45 g of a solution of 20% NaOH in methanol except where it is noted in Table I. The mixture was heated with stirring to 70°-72° C. and 13.3 g of propylene oxide was added over 15 minutes. The mixture was heated with stirring for an additional 2.25 hours at 70°-72° C. Then the stirred mixture was sparged with nitrogen (approximately 2 std cubic ft/hr) at 70°-72° C. for 1.5 hours. This removed methanol and unreacted propylene oxide. After cooling, the mixture was filtered to give 775 g (100% yield) of clear yellow polysulfide. Almost nothing was removed from the product by filtration since the sodium salts (mainly NaOH and some NaSH) coated out on the walls of the reaction vessel. The sodium salts (1.26 g) could be easily removed from the walls of the vessel since they were completely soluble in a small amount of water. However, it was found that the sodium salt residue could be left on walls of reaction vessel because it will not interfere with the next run if fresh NaOH in methanol was added.

The di-t-nonyl polysulfide obtained was analyzed for mercaptan sulfur content and observed for precipitation after prolonged storage. The results are shown in Table I.

TABLE I

| | Preparation of Stable di-t-Nonyl Polysulfide | | |
|---|---|---|---|
| | Mercaptan | Visual Observation[b] | |
| Run No. | S Content (ppm)[a] | Precipitation | Clarity |
| 1 | 15 | None Visible | Clear |
| 2 | <1 | None Visible | Clear |
| 3 | 8 | None Visible | Clear |
| 4[c] | 15 | None Visible | Clear |
| 5[c] | <1 | None Visible | Clear |

[a]Mercaptan sulfur by weight. It was determined by potentiometric titration using mercuric perchlorate.
[b]Visual observation was done 4 months after preparation.
[c]In runs 4 and 5, the NaOH in methanol also contained small amounts of water, i.e. 1.78 g of 50% aqueous solution of NaOH and 3.56 g of methanol were used.

The results of Table I clearly demonstrate that a stable, deodorized, clear-colored, and low mercaptan sulfur containing di-t-nonyl polysulfide was prepared by the inventive process. Although wishing not to be bound by theory, the base (sodium hydroxide) used in the invention converts unreacted t-nonyl mercaptan and residual H$_2$S to their salts (here, sodium salts) which react readily with the alkylene oxide (here, propylene oxide) thus producing a desired polysulfide.

EXAMPLE II

This example shows that the alkylene oxide can be added to the mixture of polysulfide and the basic inorganic catalyst prior to the heating step.

The run was carried out the same as those described in Example I except that 1,2-butylene oxide was used instead of propylene oxide and that the 20% NaOH in methanol was added to the di-t-nonyl polysulfide followed by the addition of 1,2-butylene oxide, and thereafter the mixture was heated to 70°-72° C. the results are shown in Table II.

TABLE II

| | Preparation of Stable di-t-Nonyl Polysulfide | | |
|---|---|---|---|
| | Mercaptan | Visual Observation[b] | |
| Run No. | S Content (ppm)[a] | Precipitation | Clarity |
| 6 | 10 | None Visible | Clear |

[a]See footnote a, Table I.
[b]See footnote b, Table I.

The results shown in Table II indicate that a stable polysulfide product with very low mercaptan sulfur content (10 ppm) can be obtained by heating the mixture of crude polysulfide and the basic inorganic catalyst after the alkylene oxide was added.

EXAMPLE III

This is a comparative example demonstrating that if a basic inorganic catalyst is not present in the process, the final polysulfide compound has considerable odor and mercaptan sulfur, and readily becomes cloudy due to precipitation of sulfur-containing compounds.

The run was carried out the same as the described in Example II except that NaOH in methanol was replaced by 0.4 g of triethylamine, an organic base, in the process. The results are shown in Table III.

TABLE III

| | Preparation of di-t-Nonyl Polysulfide | | |
|---|---|---|---|
| | Mercaptan | Visual Observation[b] | |
| Run No. | S Content (ppm)[a] | Precipitation | Clarity |
| 7 | 135 | Considerable | Cloudy |

[a]Mercaptan sulfur by weight, see footnote a, Table I.
[b]Visual observation was done 4 months after preparation.

Table III shows that, without the aid of a basic inorganic catalyst (NaOH in methanol), the final product had much higher mercaptan sulfur level (run 7 compared with runs 1-6) and was cloudy with a considerable amount of precipitate indicating an unstable product.

EXAMPLE IV

This example shows that a stable di-t-dodecyl polysulfide with average of 5 sulfurs can also be prepared by the invention process.

To a 5 liter 3-neck flash equipped with condenser, thermowell, and magnetic stir bar, it was added 1822 g t-dodecyl mercaptan and 9.0 g triethylamine. The solution was heated to 45° C. and then 578 g sulfur (sublimed or flowers of sulfur) was added in small portions over 45 minutes at 45° C. Hydrogen sulfide was evolved during this addition. The solution was heated with stirring at 45° C. for an additional 2.5 hours. Then a gas dispersion tube was placed in the solution and nitrogen gas was bubbled through the solution (approximately 2 std cubic ft/hr) with stirring for 4 hours at 45° C.

An aliquot (775 g) of the di-t-dodecyl polysulfide prepared above was treated with the same process described in Example II for di-t-nonyl polysulfide. The results are shown in Table IV below.

TABLE IV

| | Preparation of Stable di-t-Dodecyl Polysulfide | | |
|---|---|---|---|
| | Mercaptan | Visual Observation[b] | |
| Run No. | S Content (ppm)[a] | Precipitation | Clarity |
| 8 | 8 | None Visible | Clear |

TABLE IV-continued

| | 9 | 8 | None Visible | Clear |
|---|---|---|---|---|

[a] Mercaptan sulfur by weight, see footnote a, Table I.
[b] Visual observation was done 4 months after preparation.

The results shown in Table IV demonstrate that the inventive process can be satisfactorily used for the preparation of a stable, deodorized, and clear-colored di-t-dodecyl polysulfide having very low (8 ppm) mercaptan sulfur.

EXAMPLE V

This example illustrates 1,2-butylene oxide can be used in the inventive process to prepare a stable di-t-dodecyl polysulfide.

An aliquot (quantity shown in Table V) of the crude di-t-dodecyl polysulfide prepared by the process described in Example IV was treated with 1,2-butylene oxide in the presence or absence of NaOH in methanol using the same process described in Example II. The results are tabulated in Table V.

TABLE V
Preparation of di-t-Dodecyl Polysulfide

| Run No. | TD (g)[a] | Solution NaOH (g)[b] | 1,2-Butylene Oxide (g) | Mercaptan S content (ppm)[c] | Visual Observation[d] Precipitation | Clarity |
|---|---|---|---|---|---|---|
| 10 | 87 | 0.5 | 1.5 | <1 | None | Clear |
| 11 | 87 | 0 | 1.5 | 29 | Yes | Cloudy |
| 12 | 87 | 0.25 | 1.5 | 66 | Yes | Cloudy |
| 13 | 174 | 0[e] | 3.0 | 73 | Yes | Cloudy |
| 14 | 87 | 0.2[f] | 1.5 | 67 | Yes | Cloudy |
| 15 | 87 | 0 | 1.5[g] | 34 | Yes | Cloudy |
| 16 | 87 | 0.2[f] | 1.5[g] | 78 | Yes | Cloudy |

[a] TD is the abbreviation for di-t-dodecyl polysulfide.
[b] 20% NaOH in methanol.
[c] Mercaptan sulfur. See footnote a, Table I. The mercaptan S content of starting di-t-dodecyl polysulfide was 549 ppm.
[d] After 4 months.
[e] Though no NaOH in methanol was present, 0.4 g triethylamine was present.
[f] 0.2 g of 50% aqueous NaOH solution were used instead of 0.5 g of 20% NaOH in methanol.
[g] In this run, propylene oxide was used.

Run 10 in Table V shows that a di-t-dodecyl polysulfide having a very low sulfur content (<1 ppm) was obtained by treatment with 1,2-butylene oxide in the presence of NaOH in methanol. The mercaptan sulfur content increased significantly to 29 and 34 ppm (runs 11 and 15 respectively) if NaOH in methanol was completely omitted from the treatment process. However, decreasing the amount of NaOH in methanol also increased the mercaptan sulfur content to 66 ppm (run 12). Additionally, the inventive process (run 10) produced a final product that was stable whereas comparative runs 11, without NaOH in methanol, produced a di-t-dodecyl polysulfide that was unstable and became precipitated and cloudy upon storage.

Furthermore, replacing NaOH in methanol with an organic base (triethylamine, run 13) resulting in producing a di-t-dodecyl polysulfide having a poor stability, i.e. turning cloudy and heaving sulfur precipitation. Although an unsatisfactory result was obtained with 0.2 g of 50% aqueous NaOH solution (runs 14 and 16), satisfactory results were obtained with 20% NaOH in water for di-t-nonyl polysulfide. These results are shown in Table VI below.

TABLE VI
Preparation of Stable di-t-Nonyl Polysulfide with 20% NaOH in Water

| Run | TP (g)[a] | Base (g)[b] | PO (ml)[c] | Mercaptan S Content (ppm)[d] | Visual Observation[e] Precipitation | Clarity |
|---|---|---|---|---|---|---|
| 17 | 87 | 0.5 | 1.8 | 4.6 | None | Clear |
| 18 | 87 | 0.5 | 1.8 | 4.1 | None | Clear |
| 19 | 87 | 0.5 | 1.8 | <4.1 | None | Clear |
| 20 | 87 | 0.5 | 1.8 | 4.8 | None | Clear |

[a] TP, crude di-t-nonyl polysulfide.
[b] Base used was 20% NaOH in water.
[c] PO, propylene oxide.
[d] See footnote a, Table I.
[e] See footnote b, Table I.

EXAMPLE VI

This example demonstrates that tetramethylammonium hydroxide, together with an alkylene oxide, can be used to stabilize a crude dialkylpolysulfide.

The runs were carried out the same as those described in Example I except the quantities of the crude product and the reagents were varied as shown in Table VII.

TABLE VII
Preparation of Stable di-t-Nonyl Polysulfide Using Tetramethylammonium Hydroxide in Methanol

| Run | TP (g)[a] | Base (g)[b] | PO (ml)[c] | Mercaptan S Content (ppm)[d] | Visual Observation[e] Precipitation | Clarity |
|---|---|---|---|---|---|---|
| 21 | 174 | 2.28 | 3.6 | 23.0 | None | Clear |
| 22 | 87 | 1.14 | 1.8 | 13.0 | None | Clear |
| 23 | 87 | 1.14 | 1.8 | 6.7 | None | Clear |
| 24 | 87 | 1.14 | 1.8 | 14.0 | None | clear |
| 25 | 87 | 1.14 | 2.2 | 6.6 | None | Clear |
| 26 | 87 | 0.3[f] | 1.8 | 53.0 | None | Cloudy |

[a] TP, crude di-t-nonylpolysulfide.
[b] Base used, except run 22 which was ammonium hydroxide, was 20% tetramethylammonium hydroxide in methanol.
[c] PO, propylene oxide.
[d] See footnote a, Table I.
[e] See footnote b, Table I.
[f] Base used in run 22 was 0.3 g of concentrated ammonium hydroxid in 0.4 g methanol.

As the results in Table VII show, tetramethylammonium hydroxide was very effective in decreasing the mercaptan sulfur content in the crude di-t-nonyl polysulfide to as low as 6.7 ppm (run 23). Run 26 was inserted as control and was unsatisfactory due to being very cloudy and high mercaptan sulfur content of 53 ppm. All other runs produced satisfactory stable di-t-nonyl polysulfides.

EXAMPLE VII

This example demonstrates that water is also an effective solvent in stabilizing a dialkyl polysulfide.

The runs were carried out the same as those described in Example VI except water instead of methanol was used as solvent. The results are shown in Table VIII.

TABLE VIII
Preparation of Stable di-t-Nonyl Polysulfide Using Tetramethylammonium Hydroxide in Water

| Run | TP (g)[a] | Base (g)[b] | PO (ml)[c] | Mercaptan S Content (ppm)[d] | Visual Observation[e] Precipitation | Clarity |
|---|---|---|---|---|---|---|
| 27[f] | 87 | 1.14 | 1.8 | 12.0 | None | Clear |
| 28 | 87 | 1.14 | 1.8 | <5.0 | None | Clear |
| 29 | 87 | 0.92 | 1.8 | 6.3 | None | Clear |

TABLE VIII-continued

Preparation of Stable di-t-Nonyl Polysulfide
Using Tetramethylammonium Hydroxide in Water

| Run | TP (g)[a] | Base (g)[b] | PO (ml)[c] | Mercaptan S Content (ppm)[d] | Visual Observation[e] Precipitation | Clarity |
|---|---|---|---|---|---|---|
| 30 | 87 | 0.92 | 1.8 | 5.6 | None | clear |

[a,c,d,e]See corresponding footnotes in Table VII.
[b]Base used was tetramethylammonium hydroxide (20% in runs 27-28 and 25% in runs 29-30) in water.
[f]Run 27 was heated to 91° C. before adding propylene oxide.

The results in Table VIII clearly show that water is an effective solvent to prepare a stable polysulfide compound. The mercaptan S content was reduced to as low as <5 ppm (Run 27) and as low quantity as 0.92 g of tetramethylammonium was effective (Runs 29-30).

EXAMPLE VIII

This example illustrates that tetraethylammonium hydroxide is also effective in stabilizing a dialkyl polysulfide.

The runs were carried out the same as those described in Example VI except that tetraethylammonium hydroxide instead of tetramethylammonium hydroxide was used. The results are shown in Table IX.

TABLE IX

Preparation of Stable di-t-Nonyl Polysulfide
Using Tetraethylammonium Hydroxide

| Run | TP (g)[a] | Base (g)[b] | PPO (ml)[c] | Mercaptan S Content (ppm) | Visual Observation[e] Precipitation | Clarity |
|---|---|---|---|---|---|---|
| 27 | 87 | 1.84 | 1.8 | <5 ppm | None | Clear |

[a,c,d,e]See corresponding footnotes in Table VII.
[b]Base used was 20% tetraethylammonium hydroxide in methanol.

Table IX demonstrates that tetraethylammonium hydroxide was an effective base to reduce mercaptan S to as low as <5 ppm and to stabilize the crude product.

The results shown in the above examples clearly demonstrate that the present invention is well adapted to carry out the objects and attain the ends and advantages mentioned as well as those inherent therein. While modifications may be made those skilled in the art, such modifications are encompassed within the spirit of the present invention as defined by the disclosure and the claims.

That which is claimed is:

1. A process for stabilizing and deodorizing a polysulfide comprising contacting said polysulfide with an alkylene oxide in the presence of a basic catalyst in a solvent wherein said basic catalyst is selected from the group consisting of a tetraalkylammonium hydroxide and an inorganic base and said process is carried out at a temperature in the range of from about 50° C. to about 150° C.

2. A process according to claim 1 wherein said polysulfide is a dialkyl polysulfide having the formula of $RS_nR'$ wherein R and R' are the same or different alkyl radicals having about 1 to about 20 carbon atoms, and n is an integer of 2 to 10.

3. A process according to claim 2 wherein said R and R' each has 3 to 15 carbon atoms and n is 3 to 8.

4. A process according to claim 3 wherein said polysulfide is di-t-butyl polysulfide.

5. A process according to claim 3 wherein said polysulfide is di-t-nonyl polysulfide.

6. A process according to claim 3 wherein said polysulfide is di-t-dodecyl polysulfide.

7. A process according to claim 1 wherein said alkylene oxide is selected from the group consisting of ethylene oxide, propylene oxide, 1,2-butylene oxide, 1,3-butylene oxide, and isobutylene oxide.

8. A process according to claim 7 wherein said alkylene oxide is propylene oxide.

9. A process according to claim 7 wherein said alkylene oxide is 1,2-butylene oxide.

10. A process according to claim 1 wherein said inorganic base is selected from the group consisting of LiOH, NaOH, KOH, Ca(OH)$_2$, Mg(OH)$_2$, Na$_2$O, MgO, CaO, NaHCO$_3$, Na$_2$CO$_3$, CaCO$_3$, calcium phenoxide, barium phenoxide, R"ONa, R"SNa, R"O(CH$_2$CH$_2$O)mNa, R"S(CH$_2$CH$_2$O)mNa, and mixtures thereof; wherein R" is a C$_1$–C$_6$ alkyl radical and m is an integer between 1 and 15.

11. A process according to claim 10 wherein said inorganic base is NaOH.

12. A process according to claim 1 wherein said solvent is selected from the group consisting of methanol, ethanol, propanol, tetrahydrofuran, water and mixtures thereof.

13. A process according to claim 12 wherein said solvent is methanol.

14. A process according to claim 1 wherein said alkylene oxide is present in the range of, in terms of molar ratio of said alkylene oxide to said polysulfide, from about 0.001:1 to about 50:1.

15. A process according to claim 14 wherein said molar ratio is from 0.01:1 to 1:1.

16. A process according to claim 1 wherein said inorganic base is present in the range of, in terms of molar ratio of said inorganic base to said polysulfide, from about 0.001:1 to about 2:1.

17. A process according to claim 16 wherein said molar ratio is from 0.01:1 to 0.1:1.

18. A process according to claim 1 wherein said solvent is present in the range of, in terms of molar ratio of said solvent to said polysulfide from about 0.001:1 to about 20:1.

19. A process according to claim 18 wherein said molar ratio is from 0.02:1 to 1:1.

20. A process according to claim 1 wherein said tetraalkylammonium hydroxide is selected from the group consisting of tetramethylammonium hydroxide, tetraethylammonium hydroxide, tetrapropylammonium hydroxide and mixtures thereof.

21. A process according to claim 20 wherein said tetraalkylammonium hydroxide is tetramethylammonium hydroxide.

22. A process according to claim 20 wherein said tetraalkylammonium hydroxide is tetraethylammonium hydroxide.

23. A process for stabilizing and deodorizing a polysulfide comprising contacting said polysulfide with an alkylene oxide in the presence of a basic inorganic catalyst in a solvent wherein:
said polysulfide is a dialkyl polysulfide selected from the group consisting of di-t-nonyl polysulfide and di-t-dodecyl polysulfide;
said alkylene oxide is selected from the group consisting of ethylene oxide, propylene oxide, 1,2-butylene oxide, 1,3-butylene oxide, isobutylene oxide, and mixtures thereof; and is present in the range of, in terms of molar ratio of said alkylene oxide to said polysulfide, from about 0.001:1 to about 50:1;

said basic inorganic catalyst is selected from the group consisting of LiOH, NaOH, KOH, Ca(OH)$_2$, Mg(OH)$_2$, Na$_2$O, MgO, CaO, NaHCO$_3$, Na$_2$CO$_3$, CaCO$_3$, calcium phenoxide, barium phenoxide, R"ONa, R"SNa, R"O(CH$_2$CH$_2$O)mNa, R"O(CH$_2$CH$_2$O)mNa, and mixtures thereof; wherein R" is a C$_1$-C$_6$ alkyl radical and m is an integer between 1 and 15; and said basic inorganic catalyst is present in the range of, in terms of molar ratio of said basic inorganic catalyst to said polysulfide, from about 0.001:1 to about 2:1;

said solvent is selected from water, methanol, ethanol, propanol, tetrahydrofuran, and mixtures thereof; and said solvent is present in the range of, in terms of molar ratio of said solvent to said polysulfide, from about 0.001:1 to about 20:1; and said contacting is carried out at about 50°-150° C. for from about 10 minutes to about 10 hours.

24. A process according to claim 23 wherein said polysulfide is di-t-nonyl polysulfide; said alkylene oxide is propylene oxide; said molar ratio of said alkylene oxide to said polysulfide is from 0.01:1 to 1:1; said basic inorganic catalyst is NaOH; said molar ratio of said basic inorganic catalyst to said polysulfide is from 0.01:1 to 0.1:1; said solvent is methanol; said ratio of said solvent to said polysulfide is from 0.02:1 to 1:1; and said contacting is carried out at 65°-80° C. for 1 hour to 3 hours.

25. A process according to claim 23 wherein said polysulfide is di-t-dodecyl polysulfide; said alkylene oxide is propylene oxide; said molar ratio of said alkylene oxide to said polysulfide is from 0.01:1 to 1:1; said basic inorganic catalyst is NaOH; said molar ratio of said basic inorganic catalyst to said polysulfide is from 0.01:1 to 0.1:1; said solvent is methanol; said ratio of said solvent to said polysulfide is from 0.02:1 to 1:1; and said contacting is carried out at 65°-80° C. for 1 hour to 3 hours.

26. A process according to claim 23 wherein said polysulfide is di-t-dodecyl polysulfide; said alkylene oxide is 1,2-butylene oxide; said molar ratio of said alkylene oxide to said polysulfide is from 0.01:1 to 1:1; said basic inorganic catalyst is NaOH; said molar ratio of said basic inorganic catalyst to said polysulfide is from 0.01:1 to 0.1:1; said solvent is methanol; said ratio of said solvent to said polysulfide is from 0.02:1 to 1:1; and said contacting is carried out at 65°-80° C. for 1 hour to 3 hours.

27. A process for stabilizing and deodorizing a polysulfide comprising contacting said polysulfide with an alkylene oxide in the presence of a basic catalyst in a solvent wherein:

said polysulfide is a dialkyl polysulfide selected from the group consisting of di-t-nonyl polysulfide and di-t-dodecyl polysulfide;

said alkylene oxide is selected from the group consisting of ethylene oxide, propylene oxide, 1,2-butylene oxide, 1,3-butylene oxide, isobutylene oxide, and mixtures thereof; and is present in the range of, in terms of molar ratio of said alkylene oxide to said polysulfide, from about 0.001:1 to about 50:1;

said basic catalyst is selected from the group consisting of tetramethylammonium hydroxide, tetraethylammonium hydroxide, tetrapropylammonium hydroxide, and mixtures thereof; and said basic catalyst is present in the range of, in terms of molar ratio of said basic catalyst to said polysulfide, from about 0.001:1 to about 2:1;

said solvent is selected from water, methanol, ethanol, propanol, tetrahydrofuran, and mixtures thereof; and said solvent is present in the range of, in terms of molar ratio of said solvent to said polysulfide, from about 0.001:1 to about 20:1; and said contacting is carried out at about 50°-150° C. for from about 10 minutes to about 10 hours.

28. A process according to claim 27 wherein said polysulfide is di-t-nonyl polysulfide; said alkylene oxide is propylene oxide; said molar ratio of said alkylene oxide to said polysulfide is from 0.01:1 to 1:1; said basic catalyst is tetramethylammonium hydroxide; said molar ratio of said basic catalyst to said polysulfide is from 0.01:1 to 0.1:1; said solvent is methanol; said molar ratio of said solvent to said polysulfide is from 0.02:1 to 1:1; and said contacting is carried out at 65°-80° C. for 1 hour to 3 hours.

29. A process according to claim 27 wherein said polysulfide is di-t-dodecyl polysulfide; said alkylene oxide is propylene oxide; said molar ratio of said alkylene oxide to said polysulfide is from 0.01:1 to 1:1; said basic catalyst is tetramethylammonium hydroxide; said molar ratio of said basic catalyst to said polysulfide is from 0.01:1 to 0.1:1; said solvent is methanol; said molar ratio of said solvent to said polysulfide is from 0.02:1 to 1:1; and said contacting is carried out at 65°-80° C. for 1 hour to 3 hours.

30. A process according to claim 27 wherein said polysulfide is di-t-dodecyl polysulfide; said alkylene oxide is propylene oxide; said molar ratio of said alkylene oxide to said polysulfide is from 0.01:1 to 1:1; said basic catalyst is tetraethylammonium hydroxide; said molar ratio of said basic catalyst to said polysulfide is from 0.01:1 to 0.1:1; said solvent is methanol; said molar ratio of said solvent to said polysulfide is from 0.02:1 to 1:1; and said contacting is carried out at 65°-80° C. for 1 hour to 3 hours.

31. A process according to claim 27 wherein said polysulfide is di-t-dodecyl polysulfide; said alkylene oxide is propylene oxide; said molar ratio of said alkylene oxide to said polysulfide is from 0.01:1 to 1:1; said basic catalyst is tetramethylammonium hydroxide; said molar ratio of said basic catalyst to said polysulfide is from 0.01:1 to 0.1:1; said solvent is water; said molar ratio of said solvent to said polysulfide is from 0.02:1 to 1:1; and said contacting is carried out at 65°-80° C. for 1 hour to 3 hours.

* * * * *